US012599630B2

(12) United States Patent
Liu et al.

(10) Patent No.: US 12,599,630 B2
(45) Date of Patent: Apr. 14, 2026

(54) SERUM EXOSOME WITH HIGH OSTEOGENESIS AND HIGH ANGIOGENESIS, PREPARATION METHOD, AND APPLICATION THEREOF

(71) Applicant: Peking University School and Hospital of Stomatology, Beijing (CN)

(72) Inventors: Hao Liu, Beijing (CN); Yongsheng Zhou, Beijing (CN); Wei Li, Beijing (CN); Ranli Gu, Beijing (CN)

(73) Assignee: Peking University School and Hospital of Stomatology, Beijing (CN)

( * ) Notice: Subject to any disclaimer, the term of this patent is extended or adjusted under 35 U.S.C. 154(b) by 676 days.

(21) Appl. No.: 17/964,100

(22) Filed: Oct. 12, 2022

(65) Prior Publication Data

US 2023/0233605 A1     Jul. 27, 2023

(30) Foreign Application Priority Data

Jan. 25, 2022    (CN) .......................... 202210087192.9

(51) Int. Cl.
| | |
|---|---|
| *A61K 35/16* | (2015.01) |
| *A61K 9/127* | (2025.01) |
| *A61P 19/08* | (2006.01) |

(52) U.S. Cl.
CPC .............. *A61K 35/16* (2013.01); *A61K 9/127* (2013.01); *A61P 19/08* (2018.01)

(58) Field of Classification Search
CPC .......... A61K 35/16; A61K 9/127; A61P 19/08
See application file for complete search history.

(56) References Cited

PUBLICATIONS

Christina Coughlan et. al. (Exosome Isolation by Ultracentrifugation and Precipitation: A Comparison of Techniques for Downstream Analyses, Curr Protoc Cell Biol. Sep. 2020; 88(1)). (Year: 2020).*

Yazhou Cui et. al. (Exosomes derived from mineralizing osteoblasts promote ST2 cell osteogenic differentiation by alteration of microRNA expression, FEBS Letters 590 (2016) 185-192) (Year: 2016).*

* cited by examiner

*Primary Examiner* — Anand U Desai
*Assistant Examiner* — Jacob A Boeckelman
(74) *Attorney, Agent, or Firm* — Hemisphere Law, PLLC

(57) ABSTRACT

A serum exosome with high osteogenesis and high angiogenesis, a preparation method and an application thereof are provided, which belongs to the field of bone defect repair technologies. The serum exosome is derived from a serum in a fracture recovery period, and the fracture recovery period is in a range of a second week to a fifth week after fracture. It has been found that the exosomes extracted from the serum after fracture have stronger osteogenic and angiogenic properties than exosomes extracted from normal serum, which is helpful to solve problems that large segmental bone defects, extensive traumas and other diseases are difficult to repair, and provide a new therapy for all diseases that need to be repaired and cured through osteogenic and/or angiogenic properties.

5 Claims, 9 Drawing Sheets

SERUM EXOSOME WITH HIGH OSTEOGENESIS AND HIGH ANGIOGENESIS, PREPARATION METHOD, AND APPLICATION THEREOF

TECHNICAL FIELD

The disclosure relates to bone defect repair technologies, more particular to a serum exosome with high osteogenesis and high angiogenesis, a preparation method, and an application thereof.

BACKGROUND

Large segmental bone defects caused by tumor, infection, trauma, developmental malformation, and the like are quite common in clinic, which seriously affect life and health of patients and cause tremendous psychological burden on the patients. At present, bone marrow transplantation is a main therapy for the large segmental bone defects in clinic. However, both autogenous bone transplantation (also referred to as autogenous bone graft) and allograft bone transplantation have many shortcomings, the biggest problem is that the large segmental bone defects cannot be effectively repaired and corresponding physiological functions cannot be recovered.

Exosomes are a class of extracellular vesicles with a diameter in a range of 30 nanometers (nm) to 150 nm that are secreted by cells, which originate from endosomes formed during cellular uptake, the exosomes are finally released from cells to the outside, and then enter recipient cells through endocytosis, direct fusion or "ligand-receptor" interaction. The exosomes carry abundant bioactive molecules (such as ribonucleic acid abbreviated as RNA, protein, etc.), and can participate in the functional regulation of local or remote cells by means of autocrine or paracrine pathways, affecting extracellular microenvironments.

SUMMARY

The disclosure aims to provide a serum exosome with high osteogenesis and high angiogenesis, a preparation method, and an application thereof.

In order to realize the purposes of the disclosure, the disclosure provides technical solutions as follows.

The disclosure provides a serum exosome with high osteogenesis and high angiogenesis, and the serum exosome is derived from a serum in a fracture recovery period.

In an embodiment, the fracture recovery period is in a range of a second weeks to a fifth week after fracture.

The disclosure also provides an application/use of the serum exosome in preparing at least one of an osteogenic drug and an angiogenic drug.

In an embodiment, the at least one of the osteogenic drug and the angiogenic drug includes at least one of a bone defect repair drug and an extensive trauma repair drug.

The disclosure also provides a preparation method of the serum exosome, which includes the following steps:

step (1), collecting a blood sample during the fracture recovery period, then separating the blood sample to obtain a serum;

step (2), diluting the serum, performing solid-liquid separation on the diluted serum to obtain a supernatant; and step (3), performing solid-liquid separation on the supernatant to obtain a sediment, wherein the sediment is the serum exosome.

In an embodiment, the separating the blood sample to obtain a serum of the step (1) is performed by centrifugation, and a rotational speed of the centrifugation is in a range of 1500 revolutions per minute (rpm) to 2500 rpm, and a duration of the centrifugation is in a range of 5 minutes to 15 minutes.

In an embodiment, a diluent for the diluting the serum in the step (2) is a phosphate buffer saline (PBS) buffer, and a volume ratio of the serum to the PBS buffer is in a range of 1:8 to 1:12.

In an embodiment, the solid-liquid separation in the step (2) is performed by centrifugal separation, the centrifugal separation is performed twice comprising a first centrifugal separation and a second centrifugal separation, a rotational speed of the first centrifugal separation is in a range of 1500 gravitational acceleration (g) to 2500 g and a duration of the first centrifugal separation is in a range of 15 minutes to 25 minutes, a rotational speed of the second centrifugal separation is in a range of 8000 g to 12000 g, and a duration of the second centrifugal separation is in a range of 25 minutes to 35 minutes.

In an embodiment, the solid-liquid separation in the step (3) is performed by centrifugal separation, a rotational speed of the centrifugal separation is in a range of 8000 g to 12000 g, and a duration of the centrifugal separation is in a range of 60 minutes to 100 minutes.

The existing serum exosomes are usually derived from the serum of normal healthy people, and their ability to treat extensive traumas or large area tissue regeneration is still insufficient. It has been found that the exosomes extracted from the serum after fracture have stronger osteogenic and angiogenic properties than exosomes extracted from normal serum, which is helpful to solve problems that large bone defects, extensive traumas and other diseases are difficult to repair. It provides a new therapy for all diseases requiring osteogenic and/or angiogenic properties.

DETAILED DESCRIPTION OF EMBODIMENTS

Figure 1:
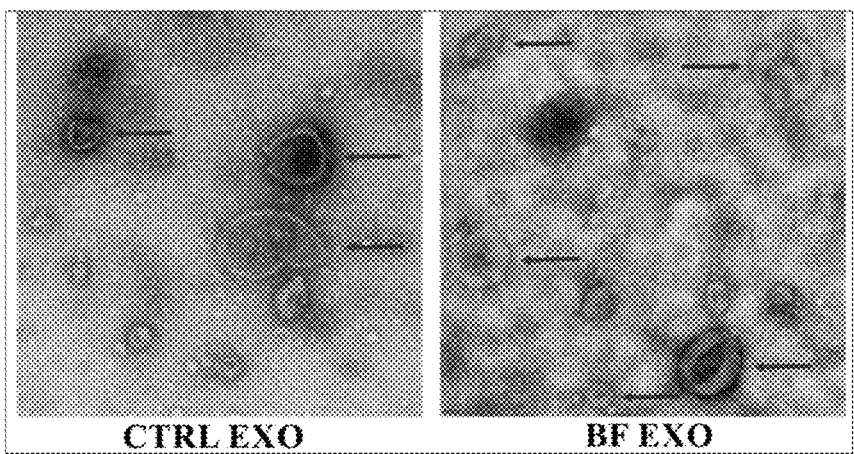
FIG. 1 illustrates a diagram of rabbit serum exosomes after fracture (BF EXO) and rabbit normal serum exosomes (CTRL EXO) by a transmission electron microscope (TEM) according to an embodiment 2.

The disclosure provides a serum exosome with high osteogenesis and high angiogenesis, and the serum exosome is derived from a serum of a recovery fracture period.

In the disclosure, the fracture recovery period is in a range of a second week to a fifth week after fracture. In an embodiment, the fracture recovery period is in a range of a third week to a fourth week after fracture.

The disclosure also provides a use of serum exosome in preparing osteogenic and/or angiogenic drugs.

In the disclosure, the osteogenic and/or angiogenic drugs are used to for therapy of bone defect repair and/or repair of extensive traumas. In an embodiment, the osteogenic and/or angiogenic drugs are used for the therapy of the bone defect repair.

The disclosure also provides a preparation method of the serum exosome, which includes the following steps:

step (1), collecting a blood sample during the fracture recovery period, then separating the blood sample to obtain a serum;

step (2), diluting the serum, performing solid-liquid separation on the diluted serum to obtain supernatant; and step (3), performing solid-liquid separation on the supernatant to obtain a sediment, wherein the sediment is the serum exosome.

In the disclosure, the fracture recovery period is in a range of a second week to a fifth week after fracture. In an embodiment, the fracture recovery period is in a range of a third week to a fourth week after fracture.

In an embodiment, the blood sample is a mixed blood sample of peripheral arterial blood collected at the second, third, fourth and fifth weeks of the fracture recovery period.

In an embodiment, the separating the blood sample to obtain a serum in the step (1) is performed by centrifugation, and a rotational speed of the centrifugation is 1500-2500 revolutions per minute (rpm), preferably 1800-2200 rpm, and a duration of the centrifugation is 5-15 minutes, preferably 10 minutes.

In an embodiment, the separated serum may be frozen when it is not used temporarily.

In an embodiment, a diluent for the diluting the serum in the step (2) is a phosphate buffer saline (PBS) buffer, and a volume ratio of the serum to the PBS buffer is 1:8-1:12, preferably 1:9-1:11, and further preferably 1:10.

In an embodiment, the solid-liquid separation in the step (2) is performed by centrifugal separation.

In an embodiment, the centrifugal separation in the step (2) is performed twice. A rotational speed of a first centrifugal separation is 1500-2500 g, preferably 1800-2300 g, and further preferably 2000 g. A duration of the first rotational speed is 15-25 minutes, preferably 18-22 minutes, and further preferably 20 minutes.

In the embodiment, a rotational speed of a second centrifugal separation in the step (2) is 8000-12000 g, preferably 1000-11000 g, and further preferably 10000 g. A duration of the second centrifugal separation is 25-35 minutes, preferably 28-22 minutes, and further preferably 20 minutes.

After the supernatant is separated, the supernatant is separated again through the solid-liquid separation, a new supernatant is removed, and a sediment is taken.

In an embodiment, the solid-liquid separation in the step (3) is centrifugal separation.

In an embodiment, a rotating speed of the centrifugal separation in the step (3) is 8000-12000 g, preferably 1000-11000 g, and further preferably 10000 g. A duration of the centrifugal separation in the step (3) is 60-100 minutes, preferably 70-90 minutes, and further preferably 80 minutes.

In an embodiment, the obtained sediment is resuspended in the PBS buffer, and centrifuged again under the centrifugation condition of the step (2). After centrifugation, the supernatant is removed, and the sediment is resuspended with PBS buffer to obtain the serum exosome suspension.

The technical solutions provided by the disclosure are described in detail below in conjunction with the embodiments, but they cannot be understood as limiting the protection scope of the disclosure.

Embodiment 1

Source of experimental samples. Specifically, peripheral arterial blood samples were collected from ears of rabbits one week after femoral fracture on the $8^{th}$ day (the second week), the $15^{th}$ day (the third week), the $22^{nd}$ day (the fourth week), and the $29^{th}$ day (the fifth week) after fracture. 20 milliliters (mL) of blood were collected each time, the blood collected in four different time periods was mixed, then centrifuged at 2000 rpm for 10 minutes, and the upper serum was taken as the extracted sample.

The serum was diluted according to the proportion of 1 mL serum to 10 mL PBS buffer solution, reversed and mixed, and then placed in a centrifuge tube for centrifugation at 2000 g and 4° C. for 20 minutes. After that, the supernatant was taken and transferred into a new centrifuge tube, and centrifuged at 10000 g and 4° C. for 30 minutes. After that, the supernatant was taken and transferred into another new centrifuge tube. After centrifugation at 10000 g and 4° C. for 80 minutes. After that, the supernatant was discarded and the sediment was resuspended with 1 mL of PBS buffer, and then centrifuged at 10000 g and 4° C. for 80 minutes. After that, the supernatant was discarded and the sediment was resuspended with 50 microliters (μL) of PBS buffer to obtain serum exosome suspension.

In this situation, the serum exosome suspension of normal rabbits (healthy rabbits without fracture) was prepared as a control according to the above method.

Embodiment 2

Identification of Two Kinds of Serum Exosomes Prepared in the Embodiment 1

Figure 2:
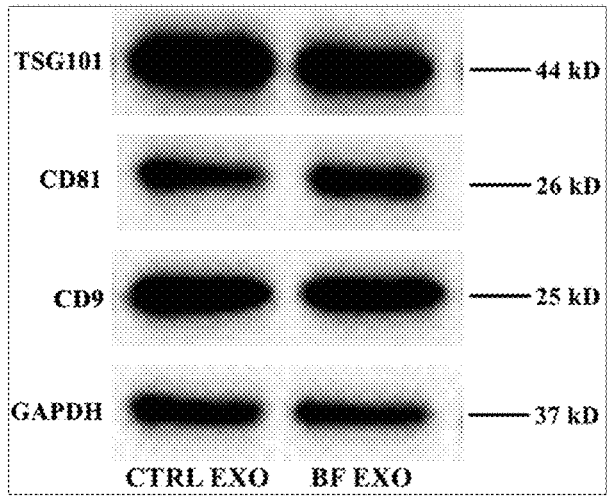
FIG. 2 illustrates an electropherogram of proteins secreted by the rabbit serum exosomes after fracture and the rabbit normal serum exosomes according to the embodiment 2.
Figure 3A:
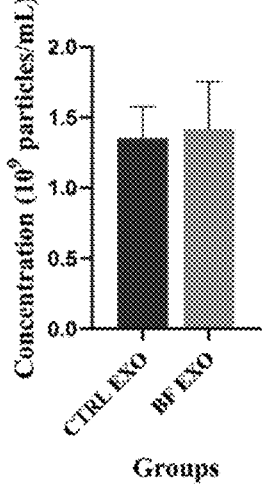
FIG. 3A illustrates a concentration distribution of the rabbit serum exosomes after fracture and the rabbit normal serum exosomes according to the embodiment 2.
Figure 3B:
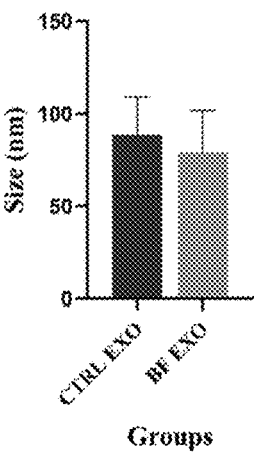
FIG. 3B illustrates a size distribution of the rabbit serum exosomes after fracture and the rabbit normal serum exosomes according to the embodiment 2.

The morphology, properties and content of exosomes were determined using a transmission electron microscope, an exosome protein marker detection and a nanoflow detector (also referred to as Flow NanoAnalyzer), and the results are shown in FIGS. 1-3. FIG. 1 illustrates the morphology of the rabbit post-fracture serum exosome (BF EXO) and the rabbit normal serum exosome (CTRL EXO), both exosomes presented typical double-layer capsule morphology. FIG. 2 illustrates exosome protein markers the two kinds of exosomes, TSG101, CD81 and CD9 were expressed in both exosomes. FIGS. 3A-3B illustrate exosome concentration and particle size of the two kinds of exosomes, there was no significant difference in the concentration and particle size of the two kinds of exosomes. In this situation, there was no significant difference in the morphology, the exosome protein markers, and the concentration and particle size of the two kinds of exosomes. It is suggested that the osteogenic and angiogenic abilities of the exosome are not caused in the change of the morphology and structure of the exosome, but by the change of the composition of the exosome.

Embodiment 3

In Vitro Osteogenesis Assay of Serum Exosomes

Bone marrow mesenchymal stem cells (BMMSCs) were co-cultured with the two kinds of exosomes (BF EXO and CTRL EXO) to detect their osteogenic markers alkaline phosphatase (ALP) and calcium nodules.

Figure 4:
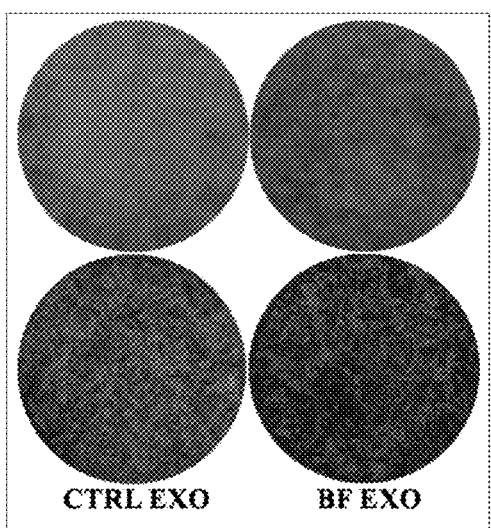
FIG. 4 illustrates results of alkaline phosphatase (ALP) staining and alizarin red staining according to an embodiment 3.
Figure 5A:
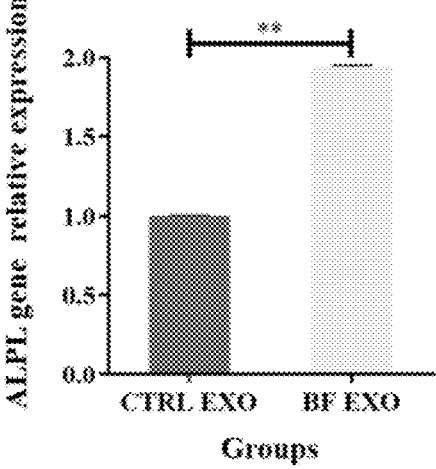
FIG. 5A illustrates a comparison of relative expression of ALP genes between a BF EXO group and a CTRL EXO group according to the embodiment 3.
Figure 5B:
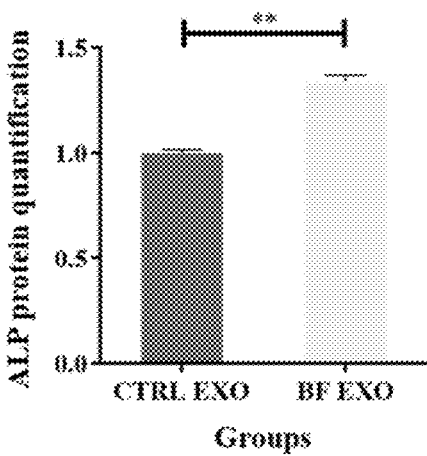
FIG. 5B illustrates a comparison of relative expression of ALP proteins between the BF EXO group and the CTRL EXO group according to the embodiment 3.

The specific methods were as follows. Specifically, osteogenic induction medium was added into a 24-well plate, 1 mL/well. Then, the BMMSCs cells were added at an inoculation density of 10000 cells/well, and then the rabbit post-fracture serum exosomes and the rabbit normal serum exosomes prepared in the embodiment 1 were added respectively, so that the final concentration was $1.69 \times 10^8$ particles/mL. The BMMSCs cells were co-cultured with the two kinds of exosomes (BF EXO and CTRL EXO) at 37° C. and 5% carbon dioxide ($CO_2$). The culture medium was changed every 3 days, and ALP staining, ALP (ALPL) gene and ALP protein detection were performed after 7 days of culture, and alizarin red staining was performed after 21 days of culture. The results of ALP staining and alizarin red staining are shown in FIG. 4, in which the left two pictures are the results of ALP staining (left upper) and alizarin red staining (left lower) in CTRL EXO group, the right two pictures are the results of ALP staining (right upper) and alizarin red staining (right lower) in BF EXO group. The results of ALP gene and ALP protein detection are shown in FIG. 5A and FIG. 5B.

The osteogenic induction medium was Dulbecco's modified eagle medium (DMEM) supplemented with 10% fetal bovine serum, 1% double antibody, 10 millimoles per liter (mM) β-glycophorophate, 10 nanomoles per liter (nM) dexamethasone, and 50 micrograms per liter (μg/mL) ascorbic acid.

The results showed that ALP staining and alizarin red staining (showing calcium nodules) in BF EXO group were darker than those in CTRL EXO group, and the relative expression of ALP (ALPL) gene and the content of ALP protein in BF EXO group were significantly higher than those in CTRL EXO group ($p < 0.01$).

Embodiment 4

Detection of Angiogenic Ability of Serum Exosomes In Vitro

Vascular endothelial cells (VECs) were cultured in vitro and co-cultured with two kinds of exosomes (BF EXO and CTRL EXO) to detect their angiogenic ability in Matrigel matrix and to evaluate the expression difference of angiogenesis-related genes in VECs.

The specific methods were as follows. Specifically, the VECs cells were amplified in vascular endothelial cell culture medium (ECM) containing 10% fetal calf serum (FBS) and 1% double antibody for 3 days. One day before the experiment, the culture medium was discarded, and the ECM containing 0.2% FBS and 1% double antibody was added for 24 hours. On the day of experiment, the VECs cells were rinsed with Dulbecco's phosphate-buffered saline (DPBS) and digested with trypsin containing ethylene diamine tetraacetic acid (EDTA). Cells were counted to a final concentration of $2 \times 10^6$ cells/mL in ECM containing 10% FBS and 1% double-antibody.

Figure 6:
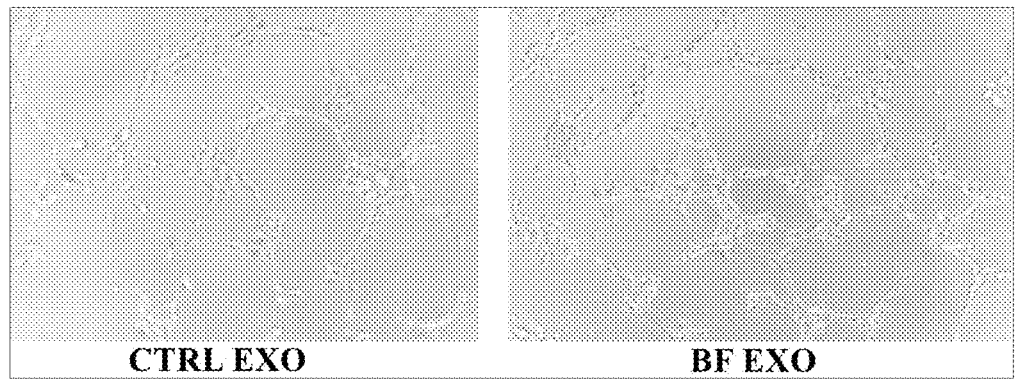
FIG. 6 illustrates in vitro angiogenesis of cardiac valvular endothelial cells (VECs) under actions of two kinds of exosomes (i.e., BF EXO and CTRL EXO) according to an embodiment 4.
Figure 7A:
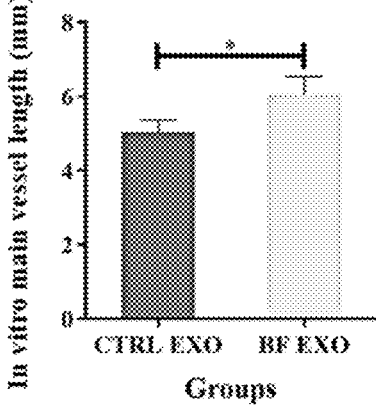
FIG. 7A illustrates a comparison of lengths of in vitro main vessels of the VECs under the actions of the two kinds of exosomes according to the embodiment 4.
Figure 7B:
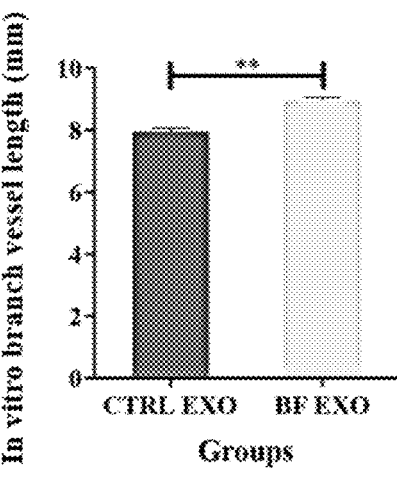
FIG. 7B illustrates a comparison of lengths of in vitro branch vessels of the VECs under the actions of the two kinds of exosomes according to the embodiment 4.

Basement membrane extract (BME), previously thawed in a refrigerator at 4° C., was added to a 96-well plate at 50 μL/well, avoiding air bubbles during pipetting and ensuring that the glue completely covered the bottom of the well. The 96-well plate was incubated at 37° C. and 5% $CO_2$ for 30 minutes to solidify the BME. The prepared 60 μL of resuspended VECs at a concentration of $2 \times 10^6$ cells/mL was mixed with 600 μL of ECM medium containing exosomes (the final concentration of exosomes after mixing with the cell suspension was $1.69 \times 10^8$ particles/mL), and then slowly and carefully added to the 96-well plate solidified with BME, 100 μL per well. The 96-well plate mixed with the VECs and the ECM medium is continued to culture in the incubator with 37° C. and 5% $CO_2$, and static culture observation. The medium was carefully removed after angiogenesis for 4 hours to avoid damaging vascular networks on BME. After washing with 100 μL of DPBS, 100 μL of fresh DPBS was added, then photographed on a white background using an inverted microscope (FIG. 6), and then vessel lengths were calculated using Image J software (FIGS. 7A-7B).

Figure 8:
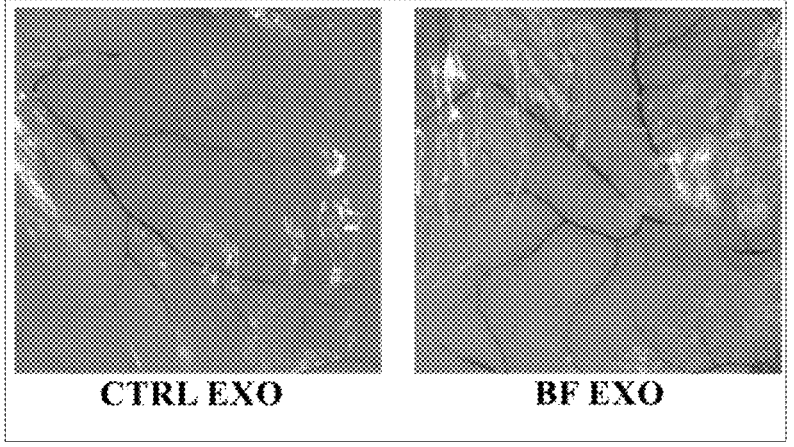
FIG. 8 illustrates in vivo angiogenesis of the VECs under the actions of the two kinds of exosomes according to the embodiment 4.
Figure 9A:
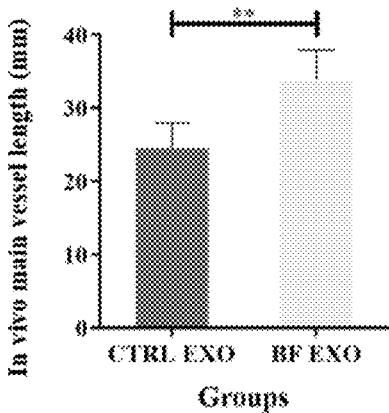
FIG. 9A illustrates a comparison of lengths of in vivo main vessels of the VECs under the actions of the two kinds of exosomes according to the embodiment 4.
Figure 9B:
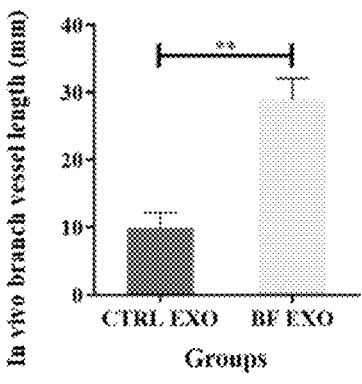
FIG. 9B illustrates a comparison of lengths of in vivo branch vessels of the VECs under the actions of the two kinds of exosomes according to the embodiment 4.
Figure 10A:
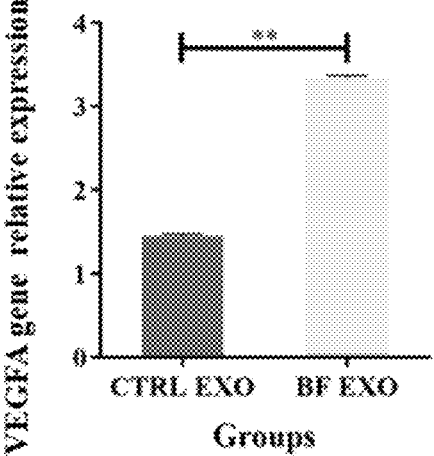
FIGS. 10A-10D illustrate relative expressions of in vivo angiogenic genes vascular endothelial growth factor A (VEGFA), vascular endothelial growth factor receptor 2 (VEGFR2), transforming growth factor beta (TGFβ), and matrix metallopeptidase 2 (MMP2) of the VECs under the actions of the two kinds of exosomes according to the embodiment 4.
Figure 10B:
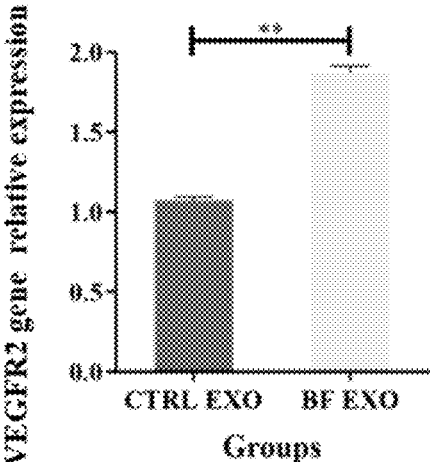
Figure 10C:
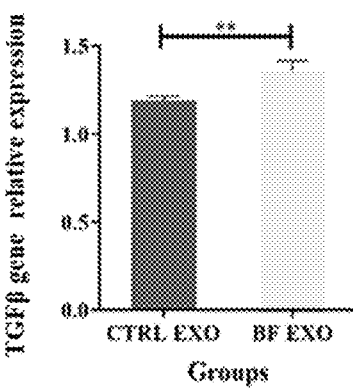
Figure 10D:
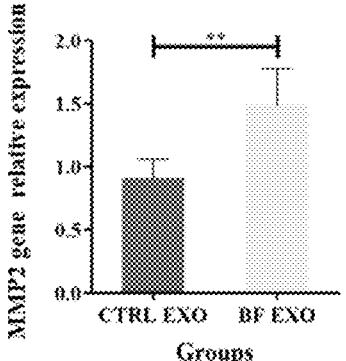

In addition, the exosomes (ECM culture medium containing exosomes with an exosome concentration of $1.69 \times 10^8$ particles/mL) and 0.5 mL of Matrigel matrix were mixed and injected subcutaneously into nude mice. One week later, the subcutaneous angiogenesis of the nude mice was observed (as shown in FIG. 8 and FIGS. 9A-9B). The relative expression of angiogenic genes vascular endothelial growth factor A (VEGFA), vascular endothelial growth factor receptor 2 (VEGFR2), transforming growth factor beta (TGFβ), and matrix metallopeptidase 2 (MMP2) were determined (as shown in FIGS. 10A-10D).

The results showed that the cyclization ability of VECs and the subcutaneous angiogenic ability of nude mice in BF EXO group were significantly higher than those in CTRL EXO group (p<0.05). Correspondingly, the relative expression of the angiogenic genes VEGFA, VEGFR2, TGFβ, and MMP2 in BF EXO group was significantly increased compared with that of CTRL EXO group (p<0.01).

Embodiment 5

Detection of Osteogenic Ability of Serum Exosomes in Repairing Rabbit Radius Defects Male New Zealand white rabbits were reared in a single cage in the General Laboratory Animal Center of Stomatological Hospital of Peking University. The rabbits were fed with special feed, drank sterile water, and had free diet; the room temperature was maintained at $21\pm2°$ C., and the living environment was maintained for 12 hours of light and 12 hours of darkness. After one week of adaptive feeding, rabbit models of large segmental bone defects (1.5 cm) in rabbit radius were made, and poloxamer gel containing two kinds of exosomes was filled at the defects, respectively.

Figure 11A:
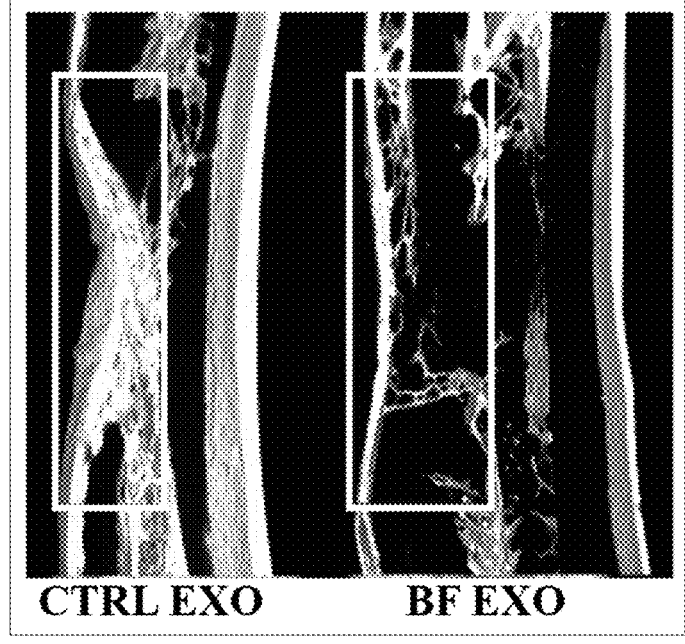
FIG. 11A illustrates a micro-CT sectional view of healing of large segmental bone defects in rabbit radii after 12 weeks of treatment with two groups of exosomes according to an embodiment 5 (regeneration areas of the rabbit radii in boxes).
Figure 11B:
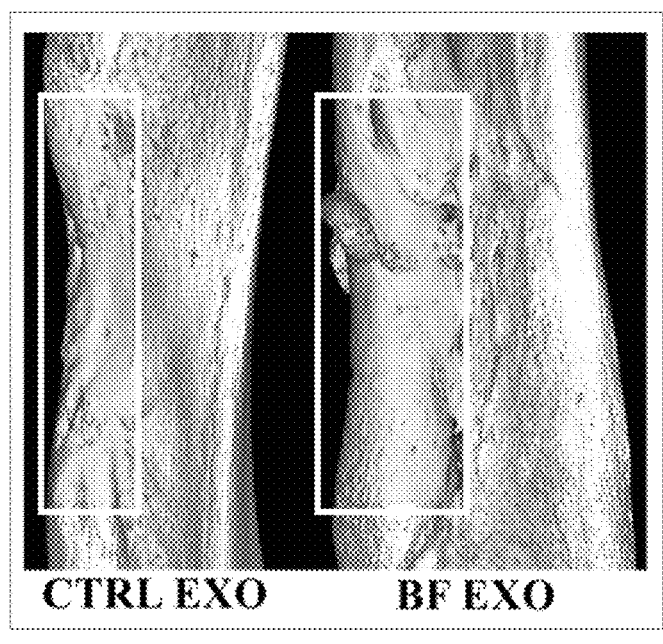
FIG. 11B illustrates a micro-CT stereoscopic view of healing of the large segmental bone defects in rabbit radii after 12 weeks of treatment with the two groups of exosomes according to the embodiment 5 (the regeneration areas of the rabbit radii in boxes).
Figure 12A:
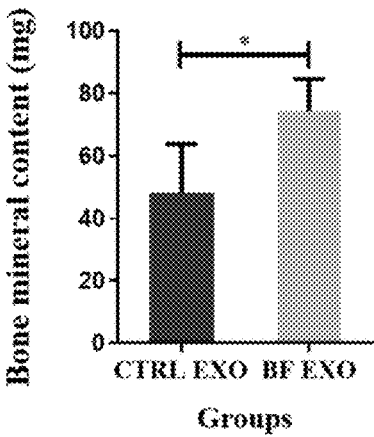
FIGS. 12A-12D illustrate comparisons of new bone parameters of the large segmental bone defect after 12 weeks of treatment with the two groups of exosomes according to the embodiment 5.
Figure 12B:
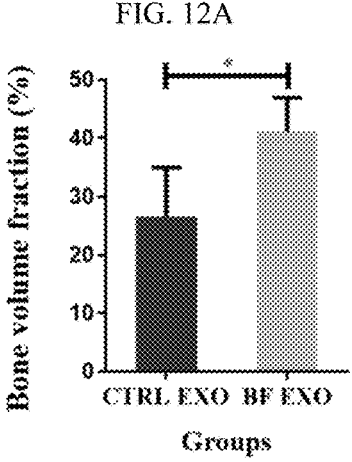
Figure 12C:
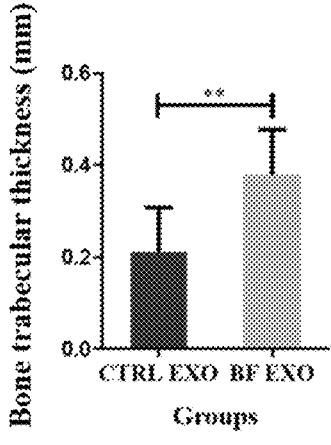
Figure 12D:
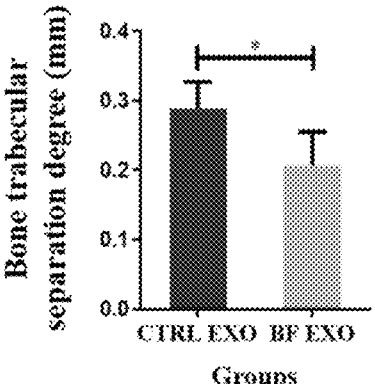

The specific methods were as follows. Rabbits were secured using a shelf and anesthetized by injecting 30 mg/kg of amobarbital sodium into the rabbit ear marginal vein. After that, the rabbit's forelimbs were prepared and disinfected, and the skin was incised with a scalpel to separate the muscle fascia and expose the radius. The length of 1.5 cm was measured and marked along the middle segment of the radius, and the radius was removed along both ends of the marked segment with a hand saw. After hemostasis by pressing with gauze, 1.5 mL of poloxamer gel containing two kinds of rabbit serum exosomes was injected into the defects, respectively (each defect contains about $6.75\times10^8$ particles of exosomes). The muscle and skin are closed and sutured layer by layer. After disinfection, the rabbits are still kept in cages under the same feeding conditions as before. After 12 weeks, the rabbits were euthanized, the radius was taken from rabbits, and the bone regeneration was detected by micro-CT (as shown in FIGS. 11A-11B). Bone mineral content, bone volume fraction, bone trabecular thickness and bone trabecular separation in the tissue were measured (as shown in FIGS. 12A-12D).

The results showed that there was bone nonunion in CTRL EXO group, while in BF EXO group, the radial canal with normal function was basically formed, and the normal bone morphology was basically restored. Moreover, bone mineral content, bone volume fraction and bone trabecular thickness in BF EXO group were significantly higher than those in CTRL EXO group (p<0.05), while bone trabecular separation in BF EXO group was significantly lower than those in CTRL EXO group (p<0.05).

Embodiment 6

Detection of Angiogenic Ability of Serum Exosomes in Repairing Rabbit Radius Defects A large segmental bone defect (1.5 cm) in the radius of the rabbit was made according to the method in the embodiment 5. In order to develop the blood vessels in the rabbit radius defect, the vessels in the bone defect were perfused with metal oxide gel before the rabbits were sacrificed at 12 weeks, and the regeneration of the blood vessels was detected by micro-CT scanning.

Figure 13:
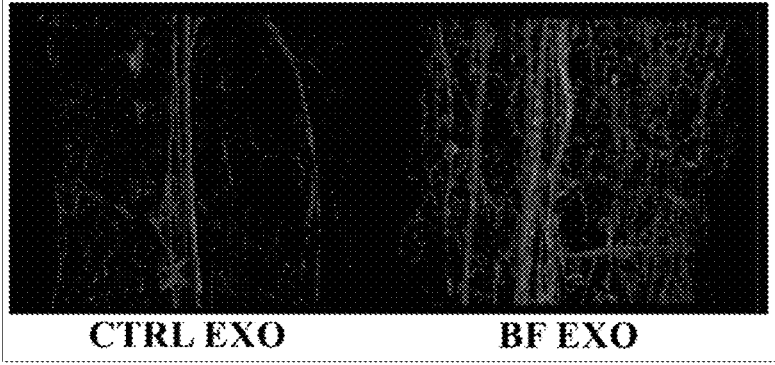
FIG. 13 illustrates a micro-CT stereoscopic view of blood vessels at bone defects in rabbit radii after 12 weeks of treatment with the two groups of exosomes according to an embodiment 6.
Figure 14A:
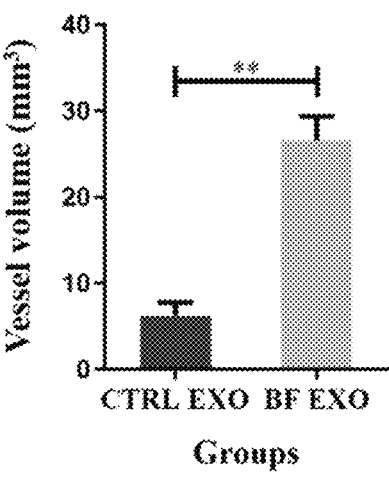
FIGS. 14A-14C illustrate comparisons of neovascularization parameters at the bone defects in rabbit radii after 12 weeks of treatment with the two groups of exosomes according to in the embodiment 6.
Figure 14B:
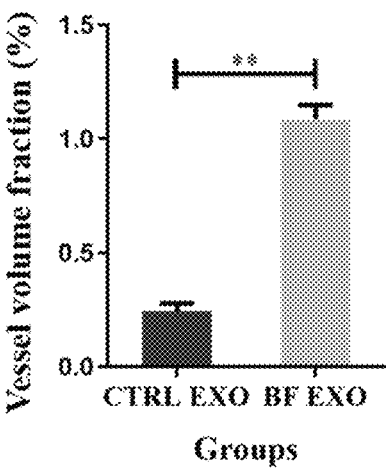
Figure 14C:
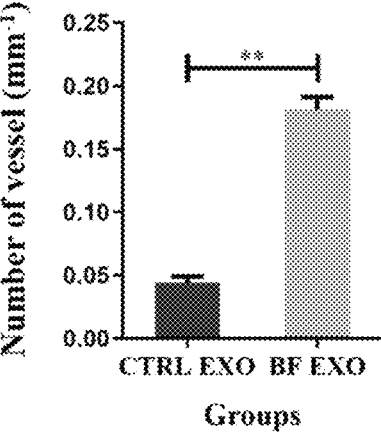

The specific methods were as follows. The rabbits were anesthetized according to the above method, the abdominal cavity and neck skin were opened, and the abdominal aorta and carotid artery were ligated in the supine position; the infusion needle was inserted into the left ventricle of the rabbit, the right atrium was cut open, and warm heparin saline solution was slowly injected to continuously rinse the vascular network of the upper limb; after the liquid from the right atrium was colorless and transparent, formalin solution was injected to fix the blood vessel; and finally, a gelatin aqueous solution containing chromium trichloride is perfused. After perfusion, the radius of the experimental side of the rabbit was taken out and placed in the refrigerator overnight to make the gel completely coagulate. Finally, the micro-CT was used to scan the rabbit radius defect, and the regeneration of blood vessels was detected after three-dimensional reconstruction (as shown in FIG. 13). The vascular volume fraction was calculated by measuring the volume and number of blood vessels (as shown in FIGS. 14A-14C).

The results showed that the volume, volume fraction and number of blood vessels in BF EXO group were significantly higher than those in CTRL EXO group (p<0.01).

The above is only the preferred embodiment of the disclosure. It should be noted that those skilled in the art may make several improvements and modifications without departing from the principle of the disclosure, and these improvements and modifications should also be considered as the protection scope of the disclosure.

What is claimed is:

1. A preparation method of a serum exosome with osteogenesis and angiogenesis derived from a serum of a fracture recovery period, comprising:
   step (1), collecting a blood sample during the fracture recovery period, then separating the blood sample to obtain a serum; wherein the fracture recovery period is in a range of a second week to a fifth week after fracture, and the blood sample is a mixed blood sample of peripheral arterial blood collected at the second, third, fourth and fifth weeks of the fracture recovery period;
   step (2), diluting the serum, performing solid-liquid separation on the diluted serum to obtain a supernatant; and
   step (3), performing solid-liquid separation on the supernatant to obtain a sediment, wherein the sediment is the serum exosome with osteogenesis and angiogenesis; and
   wherein the serum exosome is used for bone defect repair and repair of trauma.

2. The preparation method according to claim 1, wherein the separating the blood sample to obtain a serum of the step (1) is performed by centrifugation, and a rotational speed of the centrifugation is 2000 revolutions per minute (rpm), and a duration of the centrifugation is 10 minutes.

3. The preparation method according to claim 2, wherein a diluent for the diluting the serum in the step (2) is a phosphate buffer saline (PBS) buffer, and a volume ratio of the serum to the PBS buffer is 1:10.

4. The preparation method according to claim 3, wherein the solid-liquid separation in the step (2) is performed by centrifugal separation, the centrifugal separation is performed twice comprising a first centrifugal separation and a second centrifugal separation, a rotational speed of the first centrifugal separation is 2000 gravitational acceleration (g) and a duration of the first centrifugal separation is 20 minutes, a rotational speed of the second centrifugal separation is 10000 g, and a duration of the second centrifugal separation is 20 minutes.

5. The preparation method according to claim 1, wherein the solid-liquid separation in the step (3) is performed by centrifugal separation, a rotational speed of the centrifugal separation is 10000 g, and a duration of the centrifugal separation is 80 minutes.

\* \* \* \* \*